United States Patent
Hiejima et al.

(10) Patent No.: US 6,213,981 B1
(45) Date of Patent: Apr. 10, 2001

(54) SELF-ADMINISTRATION DEVICE FOR LIQUID MEDICINES

(75) Inventors: Katsuhiro Hiejima; Takeshi Mori, both of Osaka (JP)

(73) Assignee: Nissho Corporation, Osaka (JP)

( * ) Notice: Subject to any disclaimer, the term of this patent is extended or adjusted under 35 U.S.C. 154(b) by 0 days.

(21) Appl. No.: 09/256,998

(22) Filed: Feb. 25, 1999

(30) Foreign Application Priority Data

Feb. 27, 1998 (JP) .................................................. 10-064178

(51) Int. Cl.⁷ .......................... A61M 5/178; A61M 37/00; A61M 5/20
(52) U.S. Cl. ............................ 604/185; 604/134; 604/132
(58) Field of Search ................................ 604/34, 36, 131, 604/132, 134, 153, 183, 185, 212, 216, 214, 245–247, 250, 256, 891.1; 222/95, 206, 633

(56) References Cited

U.S. PATENT DOCUMENTS

| | | | |
|---|---|---|---|
| 4,236,516 | * 12/1980 | Nilson . | |
| 5,092,842 | 3/1992 | Bechtold et al. | 604/135 |
| 5,407,436 | 4/1995 | Toft et al. | 604/195 |
| 5,755,692 | * 5/1998 | Manicom | 604/152 |
| 5,807,337 | * 9/1998 | Yamada et al. | 604/143 |
| 5,891,102 | * 4/1999 | Hiejima et al. | 604/185 |

FOREIGN PATENT DOCUMENTS

| | | |
|---|---|---|
| 0 744 182 | 11/1996 | (EP) . |
| 0 744 182 A2 | 11/1996 | (EP) . |
| 0 803 206 | 10/1997 | (EP) . |
| 0 865 795 | 9/1998 | (EP) . |

* cited by examiner

Primary Examiner—John G. Weiss
Assistant Examiner—Michael J. Hayes
(74) Attorney, Agent, or Firm—Kubovcik & Kubovcik

(57) ABSTRACT

A liquid medicine self-administration device which is capable of administering a liquid medicine to a patient in a single shot and with which the refilling of the liquid medicine can be performed by a one-touch operation. The device includes a casing 1 having two open ends, a port portion 2 closing one of the open ends of the casing, a reservoir 3 attached to the port portion 2 and capable of being easily deformed by pressing and of being restored to its original shape. A pushing means 4 is slidably inserted into the other open end of the casing 1 and is adapted to press and deform the reservoir 3. The pushing means 4 comprises a cylindrical member 41 inserted into the casing 1 so as to be able to slide along the inner wall of the casing 1 and a spring 42 housed within the cylindrical member 41. The device operates such that when the cylindrical member 41 is pushed down by the pushing means 4, the cylindrical member 41 is automatically held in engagement with an engaging hook 5 while engagement of the cylindrical member 41 with the engaging hook is released by a push-button operation.

6 Claims, 7 Drawing Sheets

SELF-ADMINISTRATION DEVICE FOR LIQUID MEDICINES

BACKGROUND OF THE INVENTION

1. Field of the Invention

The present invention relates to a self-administration device for liquid medicines (hereinafter referred to as the "self-administration device") and, more particularly to such type of device that is adapted to enable a patient to inject a liquid medicine into his body by himself so to ease pain such as postoperative pain or pain caused by cancer or the like with, or without, the use of a system for continuously injecting a very small amount of a liquid medicine such as an analgesic or a narcotic.

2. Description of Related Art

Recently, in the field of anesthetics, there has been employed an epidural catheterization method using a device capable of continuously injecting a very small amount of a liquid medicine such as an analgesic to control pain such as postoperative pain, pain caused by cancer and the like. However, symptoms of patients vary and there is sometimes a case in which a patient complains of a sudden pain even in the course of continuous injection of an analgesic. In order to cope with such a critical moment, the development of a device which allows a patient to administer an analgesic to himself by a one-shot operation has been in progress. As one example of such a device, there is a liquid medicine self-administration device as described in Japanese Unexamined Patent Published Number H8-308925.

The above-described liquid medicine self-administration device comprises a cylindrical casing having an open end and a closed end provided with a liquid medicine injection port and a liquid medicine delivery port at the closed end thereof, a reservoir housed within the casing so as to cover the liquid medicine injection and delivery ports, and a pushing means mounted on the open end of the casing. This self-administration device is so constructed that when the pushing means is pressed by a patient, the reservoir is pressed by the pushing means and deformed and as a result, the liquid medicine contained in the reservoir flows through the liquid medicine delivery port.

However, the above-described prior art device has the following disadvantages when the device is used by connecting thereto a small tube such as an epidural catheter. That is, since the tube path resistance is high, force is required to deliver the liquid medicine. Further, since it takes a considerable period of time for the liquid medicine to be completely delivered, it is difficult for an enfeebled patient to continue to press the pushing means. In addition, when the pushing means is pressed with an unnecessarily strong force, there is sometimes a case in which the liquid medicine is rapidly delivered from the tip of the catheter so that the tip of the catheter moves out of position or an extremely high internal pressure is applied to the device causing the liquid medicine to leak.

SUMMARY OF THE INVENTION

The present invention has been made in view of the abovedescribed circumstances and an object of the invention is to provide a self-administration device for liquid medicines, which device is capable of administering a liquid medicine to a patient with the application of a predetermined pressure thereon, which is free from the danger of leakage of the liquid medicine and which allows the patient to perform the injection and refilling of the liquid medicine by a one-touch operation.

The above and other objects of the present invention can be achieved by providing a self-administration device comprising: a casing having both ends thereof opened; a port portion provided with liquid medicine inlet and outlet ports and closing one of the open ends of said casing; a reservoir having an open end to be closed by said port portion and a closed end, and which can be easily deformed by pressing and can be easily restored to its original shape; and pushing means for pressing and deforming said reservoir, which is slidably inserted into the other open end of said casing, and is constituted such that when said reservoir is pressed and deformed by said pushing means, a liquid medicine is delivered from said liquid medicine outlet port. The pushing means comprises a cylindrical member inserted slidably into the casing along the inner wall of the casing and a spring member housed within the cylindrical member. An engaging means is provided in the casing such that when the cylindrical member is slid toward the port portion, the engaging means automatically engages the cylindrical member at a sliding end position and can be manually released from the engaging position. By this structure, when the cylindrical member is slid toward said port portion to be brought into engagement with the port portion, the spring member is compressed and the reservoir is pressed by the spring force of the spring member.

Within the above structure, the engaging means comprises an engaging slit formed at the lower end of a skirt portion of said cylindrical member and an engaging hook formed within said casing. Further, the engaging hook comprises a split ring housed within the casing, a push-button provided on the outer peripheral surface of the split ring and projecting outwardly through a window formed in the casing, and an engaging claw being provided vertically on an upper side surface of the split ring and having an inclined surface which causes the split ring to bend inwardly when the surface is pressed by the lower end of said cylindrical member.

Further, the liquid medicine inlet and outlet ports comprises a liquid medicine inlet port connected to a liquid medicine injection tube and a liquid medicine outlet port connected to a liquid medicine delivery tube, the liquid medicine outlet port being provided with a check valve capable of blocking the inflow of the liquid medicine.

Still further, the liquid medicine inlet port and outlet port are connected to a single liquid medicine injection and delivery tube whose tip is connected to a liquid medicine injection tube and a liquid medicine delivery tube through a connector, wherein said liquid medicine delivery tube is provided with a check valve.

As described above, the present invention has the following various advantages, namely:

(1) According to a first feature of the invention, since the spring member is used as a means for pushing the reservoir, there is no fear that the reservoir is pressed by an unnecessarily strong pressing force. Since a constant force presses the reservoir, there is no fear of leakage of the liquid medicine. Further, since the pushing means is automatically held by the engaging means of the pushing means at its sliding end-position, it is sufficient for the patient to merely press the pushing means at the beginning of the injection. Further it is not necessary for the patient to continue to press the pushing means until the liquid medicine is delivered completely, so that the physical burden of the patient can be mitigated. In addition, the refilling of the liquid medicine into the reservoir can be automatically effected with a single action because when the engaging means of the pushing means is manually released, the cylindrical member moves upward by the action of the spring member and the liquid medicine is sucked into the reservoir due to the shape restoration property of the reservoir itself.

(2) According to a second feature of the invention, when the cylindrical member is pushed down, the lower end of the skirt portion of the cylindrical member presses the inclined surface of the engaging claw of the engaging hook and thereby the split ring is bent so that the engaging claw moves inside the cylindrical member and then when the engaging slit of the cylindrical member moves into a position adjacent the engaging claw, the engaging claw moves radially and outwardly to be caught by the engaging slit. Consequently, the engaging claw is automatically held in engagement with the engaging slit of the cylindrical member at the position to which the cylindrical member is slid down. Further, when the push-button is manually pressed, the split ring flexes radially and inwardly to release the engagement of the engaging claw with the engaging slit so that the cylindrical member automatically returns to its original position before it was pressed, due to the action of the spring member.

(3) Lastly, according to third and fourth features of the invention, the liquid medicine in the liquid medicine container can be filled into the reservoir through the liquid medicine inlet tube and can be injected into the catheter through the liquid medicine outlet tube. Further, due to the provision of the check valve within the liquid medicine outlet port or the connector, when the liquid medicine is refilled, the liquid medicine is allowed to flow only from the liquid medicine container into the reservoir while it is prevented from flowing from the catheter into the reservoir so that a liquid medicine refilling operation can be performed smoothly.

DETAILED DESCRIPTION OF PREFERRED EMBODIMENTS

Figure 1:
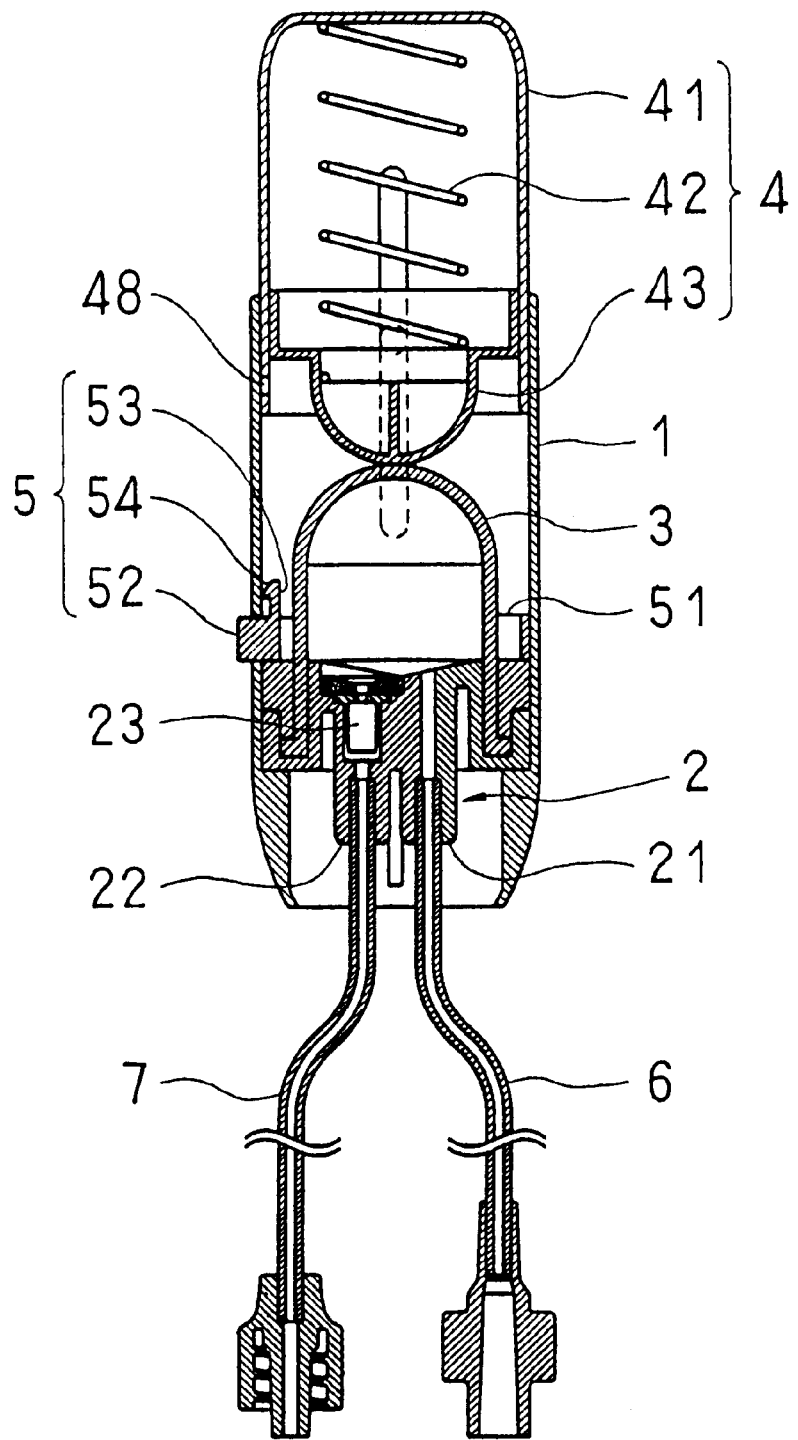
FIG. 1 is a vertical sectional view of a liquid medicine self-administration device according to one embodiment of the present invention.
Figure 2:
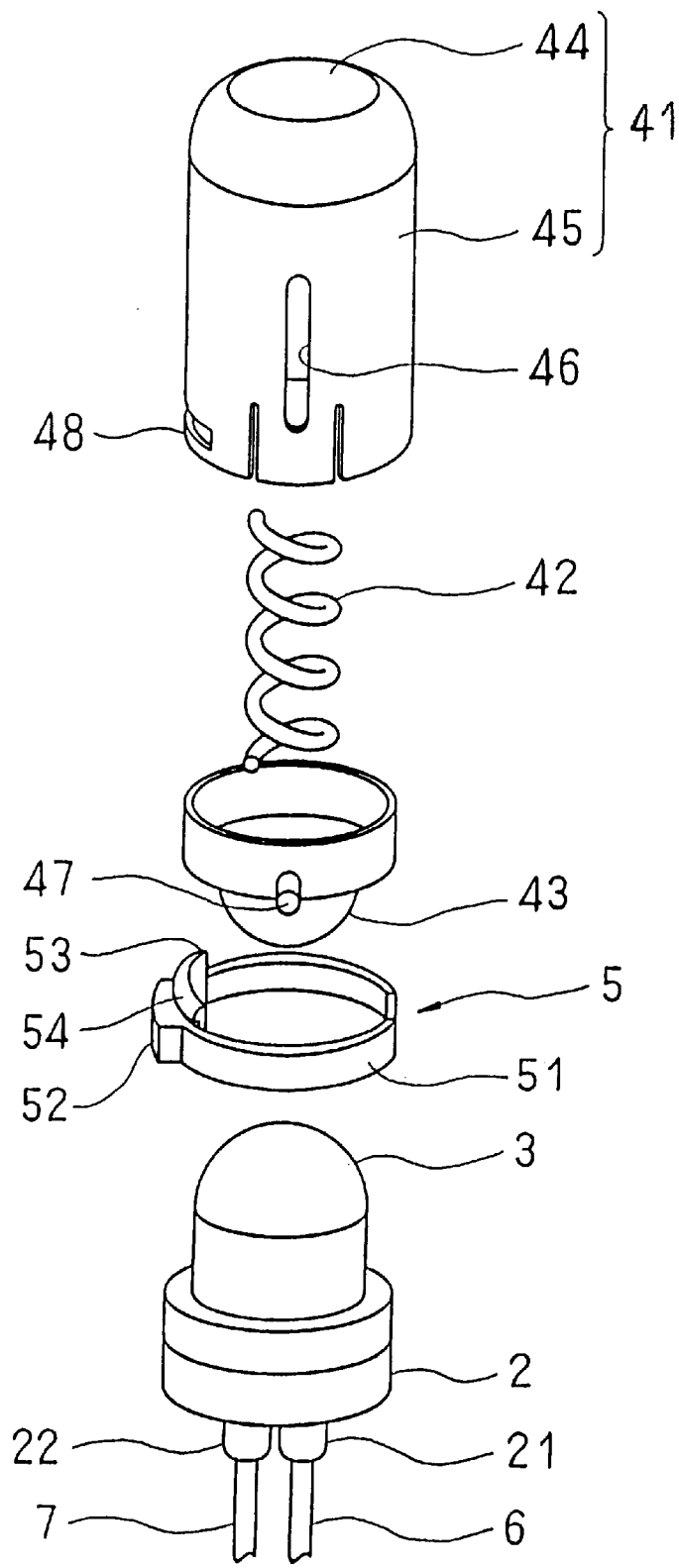
FIG. 2 is an exploded perspective view of the liquid medicine self-administration device shown in FIG. 1.

As shown in FIGS. 1 and 2, the liquid medicine self-administration device according to the present invention comprises a casing 1, a port portion 2, a reservoir 3 having an open end closed by the port portion 2 and which is easily pressure-deformable and has a shape-restoring force, and a pushing means 4 for pressure-deforming the reservoir 3.

The casing 1 is a cylindrical member made of a plastic material such as polyethylene, polypropylene, polyester, polyvinyl chloride or the like. At the port portion 2 which closes one open end of the casing 1 there are formed a liquid medicine inlet port 21 and a liquid medicine outlet port 22. Further, in the liquid medicine outlet port 22 there is provided a check valve 23 for preventing a reverse flow of the liquid medicine when the reservoir is refilled with the liquid medicine.

To the port portion 2, on the casing 1 side, there is attached the reservoir 3. This reservoir 3 is so formed as to be pressure-deformed by the pushing means 4 thereby allowing a liquid medicine contained therein to be forced outside. It is a container capable of being pressure-deformed and restored to its original shape and adapted to temporarily store the liquid medicine therein. In order to make the reservoir 3 easily deformable and shape-restorable, the reservoir 3 is formed to a thickness of 1~2 mm. Further, as materials for forming the reservoir, rubber materials such as synthetic rubbers like silicone rubber, olefin type elastomer and natural rubber are preferably used. As already described, the reservoir 3 has an open end and a closed end of which the former is closed by the port portion 2.

The pushing means 4 comprises a cylindrical member 41 inserted into the casing 1 so as to be able to slide along the inner wall of the casing 1, a spring 42 housed coaxially within the cylindrical member 41 and a pushing portion 43 attached to the tip of the spring 42.

As shown in FIG. 2, the cylindrical member 41 of the pushing means 4 has a top face 44 and a skirt portion 45. The skirt portion 45 is provided with a longitudinal slit 46 extending in the vertical (axial) direction. Further, the open end of the cylindrical member 41 is slidably inserted into the open end of the casing 1.

The spring 42 is a spring member axially housed within the cylindrical member 41. A pushing portion 43 is attached to the tip of the spring 42. The pushing portion 43 is arranged so as to be adjacent to the closed end of the reservoir 3. On the side of the pushing portion 43 there is provided a projection 47 which is movable along the longitudinal slit 46 of the cylindrical member 41. Thus, with such a structure, the cylindrical member 41 cannot rotate within the casing 1.

An engaging means which automatically holds the cylindrical member 41 at its sliding end-position or releases it from that position is constructed as follows.

At the lower end of the skirt portion 45 of the cylindrical member 41 there is formed an engaging slit 48. Within the casing 1 there is provided an engaging hook 5 arranged so as to be adjacent to the upper surface of the port portion 2 and to surround the reservoir 3. The engaging hook 5 comprises a split ring 51, a push-button 52 formed at the central portion of the circumference of the split ring 51 and an engaging claw 53 provided vertically on the upper side surface of the central portion of the split ring 51.

Further, the engaging claw 53 has an inclined surface 54 on the outer side thereof and the push-button 52 projects outwardly of a window 11 (see FIG. 3) formed at the lower end of the casing 1.

When the cylindrical member 41 is pushed down, the lower edge of the cylindrical member 41 pushes the inclined surface 54 of the engaging claw 53 so that the split ring 51 is bent inwardly to cause the engaging claw 53 to move radially inwardly thereby allowing the cylindrical member 41 to be pushed down to its sliding end-position. Then, in the above state, the engaging claw 53 engages the engaging slit 48 of the cylindrical member 41 to thereby hold the cylindrical member 41 at its sliding end-position. In this case, when a patient presses the push-button 52, the split ring 51 bends and the engaging claw 53 is disengaged from the engaging slit 48 of the cylindrical member 41 so that the cylindrical member 41 is pushed back to its original position due to the repulsive force of the spring 42 incorporated in the cylindrical member 41.

Figure 3:
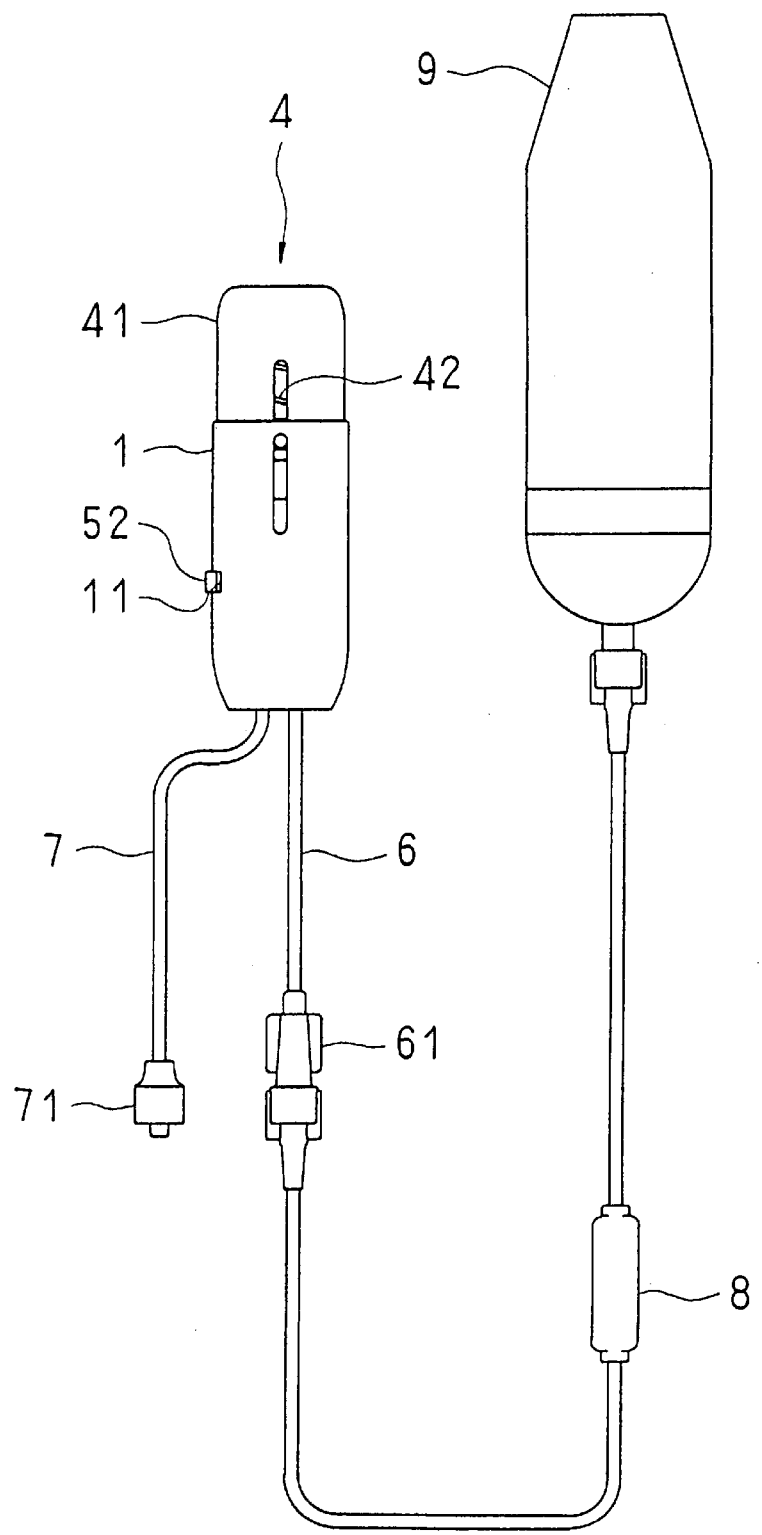
FIG. 3 is a view illustrating a manner of using the self-administration device shown in FIG. 1 when a liquid medicine container is connected to the device through a flow rate control means.

The liquid medicine inlet port 21 and the liquid medicine outlet port 22 of the port portion 2 open in the reservoir 3. To the ports 21 and 22 there are connected a liquid medicine injection tube 6 and a liquid medicine delivery tube 7, respectively. Further, as shown in FIG. 3, a liquid medicine container 9 can be connected directly or through a flow rate control means 8 to a connector 61 provided at the liquid medicine injection tube 6 and a catheter (not shown) or the like tube can be connected to a connector 71 for the liquid medicine delivery tube 7.

FIG. 1 shows a state of the liquid medicine self-administration device before pressing the pushing means 4. The cylindrical member 41 is made movable within the casing 1. When the projection 47 (see FIG. 2) moves along the longitudinal slit 46 (see FIG. 2) of the casing 1 to reach the upper end of the slit 46, the downward sliding of the cylindrical member 41 is limited. In this state, the spring 42 of the pushing means 4 is somewhat contracted due to the restoring force of the reservoir 3 and the pressure of the liquid medicine flowing from the liquid medicine inlet port 21 (see FIG. 4(a)). When the self-administration device is connected to a liquid medicine container 9 and a flow rate control means 8 as shown in FIG. 3, the amount of the liquid medicine to be injected into the body of a patient is controlled to a suitable flow rate by the flow rate control means 8.

Next, a method of using the self-administration device according to the instant embodiment will be described.

Figure 4A:
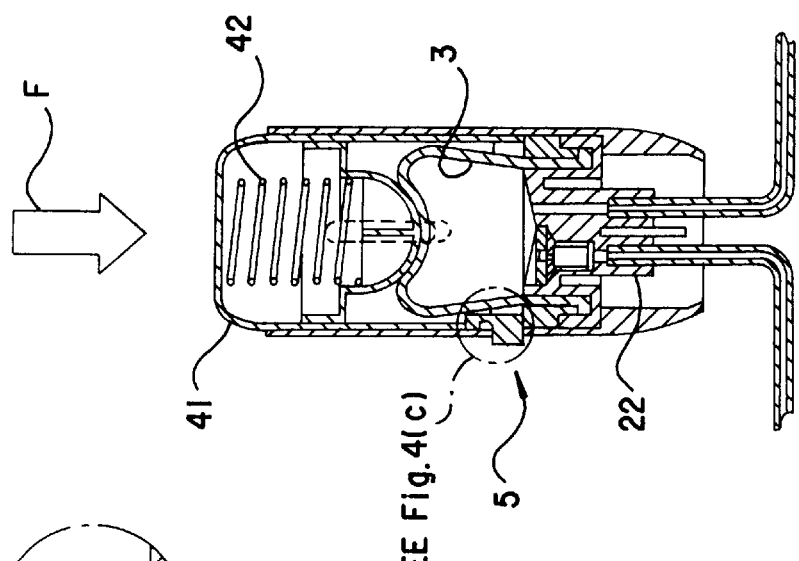
FIGS. 4a and 4b, 4c are views illustrating how a liquid medicine injecting operation is performed using the self-administration device shown in FIG. 1.
Figure 4C:
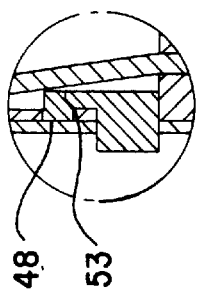

When the pushing means 4 is pressed in the direction of the arrow F from the state in which the pushing means 4 is not in use as shown in FIG. 4(a), the engaging claw 53 of the engaging hook 5 engages the engaging slit 48 of the cylindrical member 41 so that the cylindrical member 41 is held in a state in which it has reached its sliding end-position. In this state, the liquid medicine within the reservoir 3 does not flow out rapidly from the liquid medicine outlet port 22 so that the spring 42 is compressed. The reservoir 3 is maintained under compression by the spring 42 tending to expand and the liquid medicine stored in the reservoir 3 continues to be delivered from the liquid medicine outlet port 22.

Figure 4B:
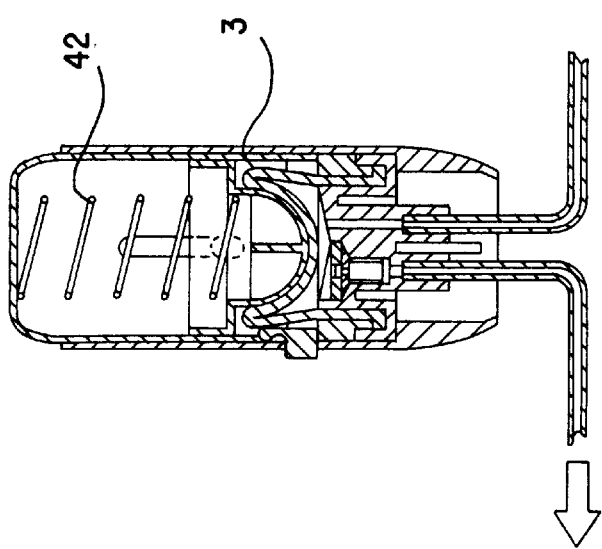

Consequently, it is sufficient for the patient to merely press down the pushing means 4 once. In this case, since the reservoir 3 is pressed at a constant pressure, there is no fear of leakage of the liquid medicine. FIG. 4(b) shows a state in which the liquid medicine has been completely delivered and in this state, the reservoir 3 is pushed in and the spring 42 is expanding.

Figure 5A:
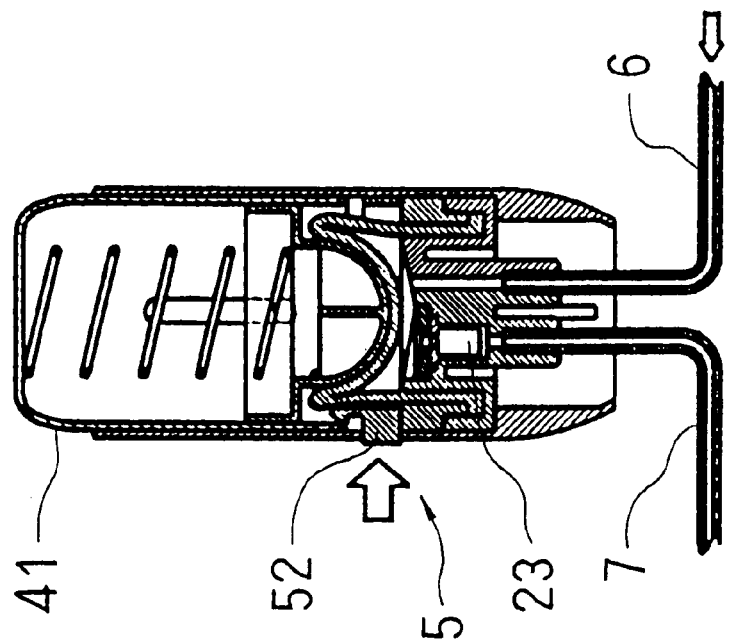
FIGS. 5a and 5b are views illustrating how a liquid medicine refilling operation is performed using the self-administration device shown in FIG. 1.
Figure 5B:
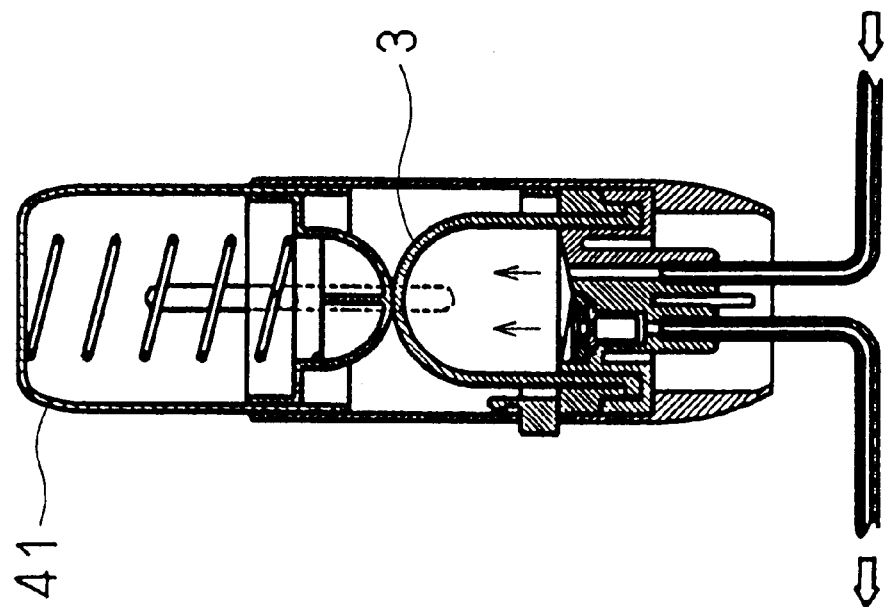
Figure 6:
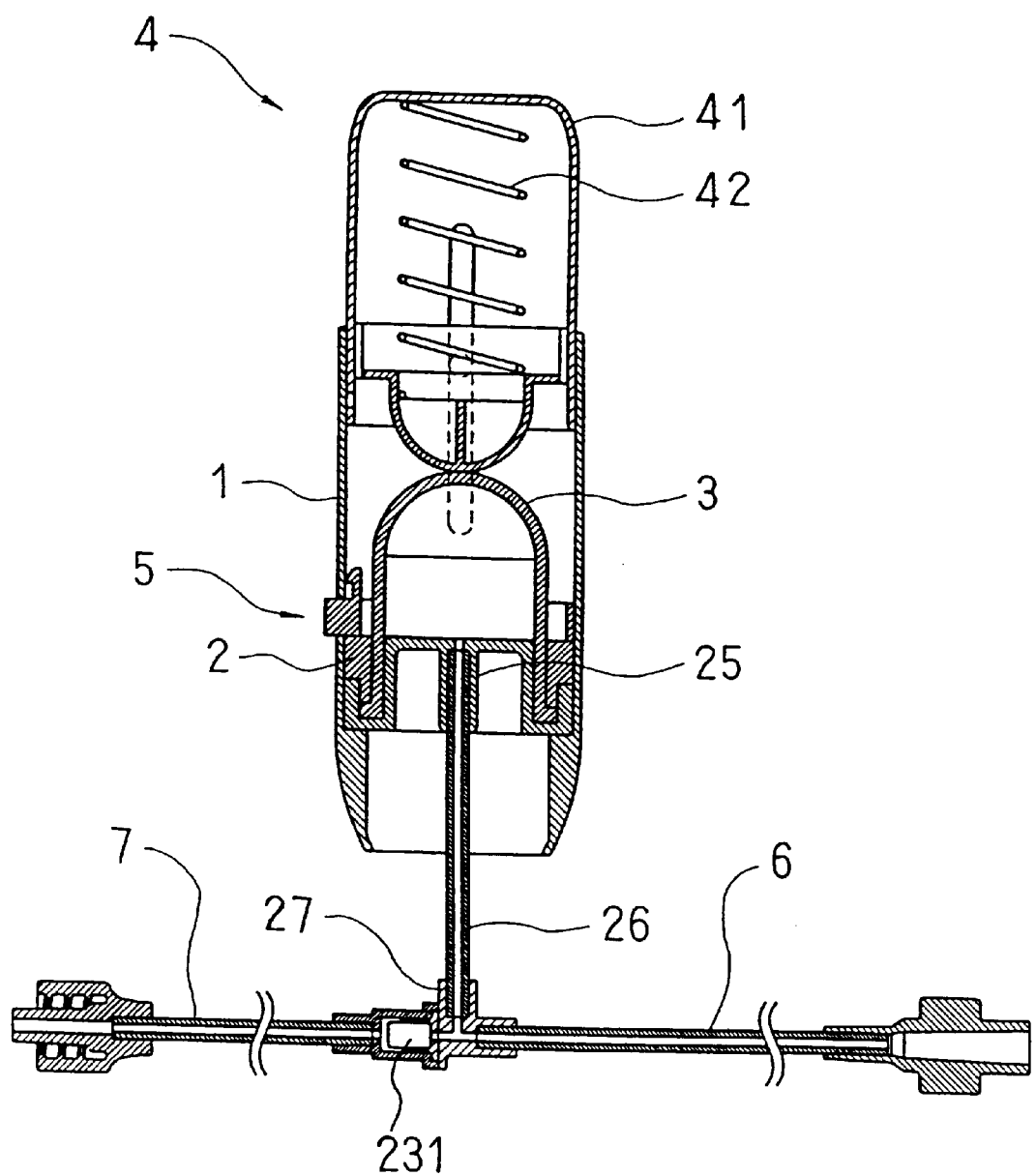
FIG. 6 is a vertical sectional view of a liquid medicine self-administration device according to another embodiment of the present invention.
Figure 7:
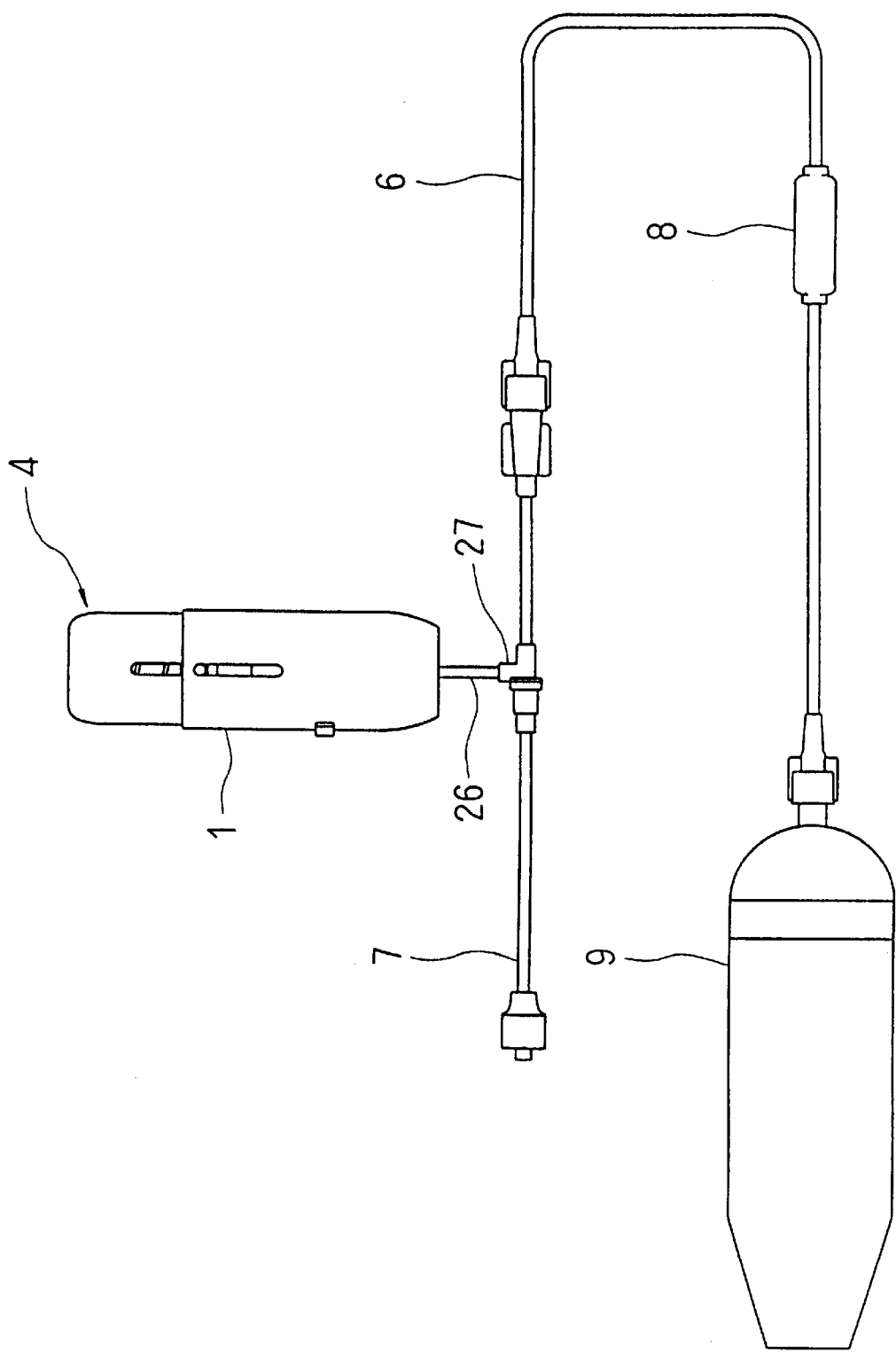
FIG. 7 is a view illustrating a manner of using the self-administration device shown in FIG. 6 when a liquid medicine container is connected to the device through a flow rate control means.

Next, in order to refill the liquid medicine into the reservoir 3 after the completion of delivery of the liquid medicine, the patient may press the push-button 52 by hand as shown by the arrow in FIG. 5(a). When the push-button is pressed the cylindrical member 41 is released from the engaging hook 5 so that the reservoir 3 expands as it pushes the cylindrical member 41 upward as shown in FIG. 5(b) due to its shape-restoring force and pulls in the liquid medicine through the liquid medicine injection tube 6. In this case, there is no reversed flow of the liquid medicine from the liquid medicine delivery tube 7 because of the presence of the check valve 23. Consequently, the refilling of the liquid medicine can be performed by a single action.

Next, a liquid medicine self-administration device according to another embodiment of the present invention will be described.

According to this embodiment, a liquid medicine inlet and outlet port 25 is so formed that the inflow and outflow of a liquid medicine are commonly effected therethrough. To this liquid medicine common port 25 there is connected a single liquid medicine injection and delivery tube 26 and the liquid medicine injection tube 6 and the liquid medicine delivery tube 7 are connected to the tip of the liquid medicine injection and delivery tube 26 through a connector 27. Further, a check valve 231 is provided in the liquid medicine delivery tube 7.

With the exception of the above-described arrangement, the remaining structure of the self-administration device according to the instant embodiment is the same as that according to the embodiment shown in FIGS. 1 and 2.

It should be noted that also in this second embodiment, the administration of the liquid medicine can be performed by merely pressing the pushing means 4 and the refilling of the liquid medicine can be performed by merely pressing the push-button 52.

Effects of the Invention

A first effect of the liquid medicine self-administration device according to the present invention is that there is no fear of leakage of the liquid medicine and the patient is not required to continuously press the pushing means. Thus, the physical burden on the patient can be mitigated and the refilling of the liquid medicine into the reservoir can also be automatically performed by a single shot.

A second effect of the liquid medicine self-administration device according to the present invention is that the cylindrical member is automatically held in engagement with the port portion at the sliding end position to which the cylindrical member is pushed and further that upon pressing the push-button manually, the cylindrical member is returned to its original position thereby allowing the refilling of the liquid medicine to be performed.

A third effect of the liquid medicine self-administration device according to the present invention is that when the liquid medicine is refilled into the reservoir, only the flow of the liquid medicine into the reservoir occurs while flow of the liquid medicine into the reservoir from the catheter is prevented so that the refilling operation can be performed smoothly.

What is claimed is:

1. A liquid medicine self-administration device comprising: a casing having first and second opened ends;
a port portion having a liquid medicine inlet port and a liquid medicine outlet port and closing the first open end of said casing;
a reservoir having an open end attached to and closed by said port portion and a closed end, said reservoir being easily deformed by pressing and being easily restored to its original shape;
pushing means for pressing and deforming said reservoir such that when said reservoir is pressed and deformed by said pushing means, a liquid medicine is delivered from said liquid medicine outlet port, said pushing means comprising a cylindrical member having a closed end and an open end, the open end of the cylindrical member being slidably inserted into the second open end of said casing along the inner wall of said casing; a spring member having first and second ends and housed within said cylindrical member, the first end of said spring being adjacent the closed end of said cylindrical member; and a pushing portion attached to the second end of said spring member and arranged to contact the closed end of said reservoir; and engaging means provided in said casing such that when said cylindrical member is slid toward said port portion, said engaging means automatically engages said cylindrical member at a sliding end position and can be manually released from the engaging position, whereby when said cylindrical member is slid toward said port portion to be brought into engagement with said engaging means, said spring member is compressed and said pushing portion presses the reservoir by the spring force of said spring member.

2. The liquid medicine self-administration device according to claim 1, wherein said engaging means comprises:

an engaging slit formed at a lower end of a skirt portion of said cylindrical member;

an engaging hook formed adjacent to said port portion within said casing and comprising:

a split ring housed within said casing, a push-button being provided on the outer peripheral surface of said split ring and which is arranged to project outwardly through a window formed in said casing; and an engaging claw provided vertically on an upper side surface of said split ring, wherein said engaging claw has an inclined surface which causes said split ring to bend inwardly when said surface is pressed by the lower end of said cylindrical member.

3. The liquid medicine self-administration device according to claim 2, wherein said liquid medicine inlet port is connected to a liquid medicine injection tube and said liquid medicine outlet port is connected to a liquid medicine delivery tube, and wherein said liquid medicine outlet port is provided with a check valve capable of blocking the inflow of liquid medicine.

4. The liquid medicine self-administration device according to claim 2, wherein said liquid medicine inlet and outlet port comprise a single port connected to a liquid medicine injection and delivery tube, a distal end of said liquid medicine injection and delivery tube being connected to a liquid medicine injection tube and a liquid medicine delivery tube through a connector, and wherein said liquid medicine injection and delivery tube is provided with a check valve.

5. The liquid medicine self-administration device according to claim 1, wherein said liquid medicine inlet port is connected to a liquid medicine injection tube and said liquid medicine outlet port is connected to a liquid medicine delivery tube, and wherein said liquid medicine outlet port is provided with a check valve capable of blocking the inflow of liquid medicine.

6. The liquid medicine self-administration device according to claim 1, wherein said liquid medicine inlet and outlet port comprise a single port connected to a liquid medicine injection and delivery tube, a distal end of said liquid medicine injection and delivery tube being connected to a liquid medicine injection tube and a liquid medicine delivery tube through a connector, and wherein said liquid medicine injection and delivery tube is provided with a check valve.

* * * * *